(12) United States Patent
Wu et al.

(10) Patent No.: US 11,040,020 B2
(45) Date of Patent: Jun. 22, 2021

(54) SULFONAMIDE PHARMACEUTICAL COMPOSITION

(71) Applicant: TIANJIN HONGRI JIAN DA KANG MEDICAL TECHNOLOGY CO., LTD, Tianjin (CN)

(72) Inventors: Yi Juang Wu, Tianjin (CN); Xiaoqing Yao, Tianjin (CN); Changhai Sun, Tianjin (CN); Li Tian, Tianjin (CN); Xinying Zhao, Tianjin (CN); Zhidong Han, Tianjin (CN); Chuangyu Lin, Tianjin (CN)

(73) Assignee: TIANJIN HONGRI JIAN DA KANG MEDICAL TECHNOLOGY CO., LTD, Tianjin (CN)

( * ) Notice: Subject to any disclaimer, the term of this patent is extended or adjusted under 35 U.S.C. 154(b) by 35 days.

(21) Appl. No.: 16/377,428

(22) Filed: Apr. 8, 2019

(65) Prior Publication Data
US 2019/0231721 A1 Aug. 1, 2019

Related U.S. Application Data

(63) Continuation of application No. 15/541,776, filed as application No. PCT/CN2016/070015 on Jan. 4, 2016, now abandoned.

(30) Foreign Application Priority Data
Jan. 6, 2015 (CN) .......................... 201510005995.5

(51) Int. Cl.
*A61K 31/18* (2006.01)
*A61K 47/10* (2017.01)
*A61K 47/12* (2006.01)
*A61K 9/00* (2006.01)
*A61K 47/20* (2006.01)
*A61K 9/08* (2006.01)
*A61K 47/34* (2017.01)
*A61P 35/00* (2006.01)

(52) U.S. Cl.
CPC ............. *A61K 31/18* (2013.01); *A61K 9/0019* (2013.01); *A61K 9/08* (2013.01); *A61K 47/10* (2013.01); *A61K 47/12* (2013.01); *A61K 47/20* (2013.01); *A61K 47/34* (2013.01); *A61P 35/00* (2018.01)

(58) Field of Classification Search
CPC ........ A61K 31/18; A61K 47/10; A61K 47/12; A61K 47/20
See application file for complete search history.

(56) References Cited

U.S. PATENT DOCUMENTS 5,891,454 A * 4/1999 Wu ...................... A61K 9/0019
424/423

FOREIGN PATENT DOCUMENTS

CN       1204511 A  *  1/1999

* cited by examiner

*Primary Examiner* — Timothy P Thomas
(74) *Attorney, Agent, or Firm* — Law Offices of Albert Wai-Kit Chan, PLLC

(57) ABSTRACT

A sulfonamide pharmaceutical composition. The present invention relates to a sulfonamide compound injectable preparation comprising a sulfonamide compound or a derivative thereof. The injectable preparation is prepared from the sulfonamide compound and a pharmaceutically acceptable carrier through certain preparation technologies. The sulfonamide compound injectable preparation involved in the present invention is stable and controllable in quality and effective.

1 Claim, No Drawings

SULFONAMIDE PHARMACEUTICAL COMPOSITION

FIELD OF THE INVENTION

This invention relates to a sulfonamide pharmaceutical composition, and their preparation and use in the pharmaceutical industry.

BACKGROUND OF THE INVENTION

Cancer is a common disease in the world today. Most cancers are diagnosed at late stage and the cure rate is low. Most of the current anticancer drugs have toxic side effects including hair loss, vomiting, decrease of white blood cell count, bone marrow suppression, and decrease in immune system function. The major reason is that these drugs act on part of the cell metabolic cycle, and they do not selectively target cancer cells as opposed to healthy cells. When they kill cancer cells, they also damage healthy cells, especially those healthy cells that are undergoing rapid metabolism.

Sulfonamide compounds have been clinically used as an antimicrobial for decades. Today, they are still one of the most commonly used antimicrobials, second only to antibiotics because of their broad antibacterial spectrum, stability, ease of use, and low price. As more in-depth studies are conducted, researchers have found that sulfonamide compounds have a wider range of biological activities, including its diuretic effect, anti-thyroid effect, anti-diabetic effect, anti-hypoglycemic effect, and its ability to treat cataract. In recent years, a large number of sulfonamide compounds with anti-tumor activity have been reported, and many among them have entered clinical trials. These compounds act on different molecular targets and exhibit significant biological activity. Some compounds exhibit high selectivity and specificity for different targets.

The mechanisms for the actions of these sulfonamide compounds are diverse, including disrupting tubulin polymerization, blocking normal cell cycle, inhibiting carbonic anhydrase, inhibiting folic acid dependent enzymes, inhibiting methionine aminopeptidase and histone deacetylase, and inhibiting vascular endothelial cell growth factor and so on.

Chinese Patent ZL97108988.4 disclosed the formulation and method to prepare injections of sulfonamide compounds.

The compounds include:

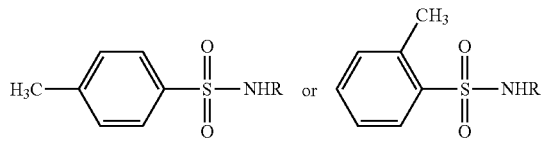

wherein R=H, $C_2H_5$, or

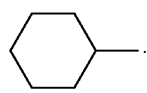

Preferably, sulfonamide compounds are selected from:

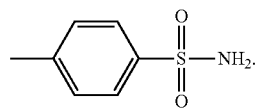

The formulation is as follows:

| | |
|---|---|
| Said sulfonamide compound | 10%~80% |
| PEG-400 | 10%~60% |
| 1,2-propanediol | 5%~30% |
| Suberic acid | 1%~20% |
| p-Toluenesulfonic acid | 1%~15% |
| Dimethyl sulfoxide | 0%~20% |
| Ethanol | 0%~20%. |

When using the above formulation to prepare p-toluenesulfonamide injections, it was accidently discovered that the above formulation has low stability, tends to crystallize after long storage time, and it also causes severe irritation to the injection site.

Studies on the formulation and preparation method above showed that the problems are caused by suberic acid and p-toluenesulfonic acid. This invention effectively solved the problems by replacing suberic acid with sebacic acid, and replacing p-toluenesulfonic acid with 2-ethyl-1, 3-hexanediol.

DETAILED DESCRIPTION OF THE INVENTION

The present invention solves the problems of low solubility and ease of crystallization associated with known injection formulations by improving the formulation and method to prepare injections of sulfonamide compounds. Comparative toxicity test also shows that the present formulation is less toxic and safer for clinical use.

The goal of this invention is to provide an injection formulation comprising a sulfonamide compound, made with the following raw materials:

| Raw Materials | Percentage by weight |
|---|---|
| Sulfonamide compound | 20%-40% |
| PEG-400 | 20%-40% |
| 1,2-propanediol | 5%-10% |
| Sebacic acid | 2%-5% |
| 2-ethyl-1,3-hexanediol | 10%-20% |
| Dimethyl sulfoxide | 0-10% |
| Anhydrous ethanol | 0-10%. |

Among polyethylene glycol-400 (PEG-400), 1,2-propanediol, sebacic acid, 2-ethyl-1, 3-hexanediol, dimethyl sulfoxide and ethanol, only dimethyl sulfoxide and ethanol are dispensable, others are required.

The sulfonamide compound is selected from one, or a mixture of two or more, at any ratio, of the following:

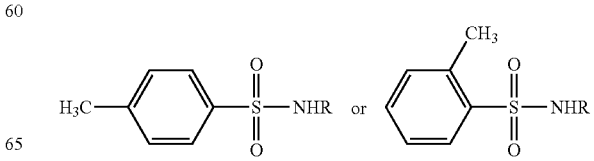

wherein R=H, C$_2$H$_5$, or

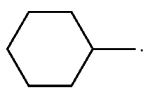

Preferably, the sulfonamide compound is selected from:

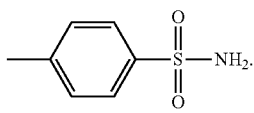

Preferably, the injection formulation of the present invention is prepared from the following raw materials:

| Raw materials | Percentage by weight |
| --- | --- |
| P-Toluenesulfonamide | 20-40% |
| PEG-400 | 20-40% |
| 1,2-propanediol | 5-10% |
| Sebacic acid | 2-5% |
| 2-ethyl-1,3-hexanediol | 10-20% |
| Dimethyl sulfoxide | 0-10% |
| Anhydrous ethanol | 0-10% |

Further preferred, the injection formulation of this invention is prepared from the following raw materials:

| Raw materials | Percentage by weight |
| --- | --- |
| p-Toluenesulfonamide | 30% |
| PEG-400 | 30% |
| 1,2-propanediol | 8% |
| Sebacic acid | 4% |
| 2-ethyl-1,3-hexanediol | 15% |
| Dimethyl sulfoxide | 5% |
| Anhydrous ethanol | 8%. |

The present invention improves upon the known injection formulations by removing suberic acid and adding the solubilizer 2-ethyl-1, 3-hexanediol. The combination of PEG-400, 2-ethyl-1, 3-hexanediol, and 1, 2-propanediol can decrease the amount of 1,2-propanediol in the injection formulation, thereby decreasing irritation at the injection site.

Another goal of this invention is to provide a method to prepare the injection.

The preparation of the injection of this invention comprises the following steps:
1) Putting a prescription amount of sulfonamide compound, PEG-400, and 2-ethyl-1, 3-hexanediol into a container, stirring slowly at 85° C.-95° C. to form a miscible solution, Solution A, for later use;
2) Putting a prescription amount of sebacic acid and 1,2-propanediol, into a separate container, stirring slowly at 85° C.-95° C. to form a miscible solution, Solution B, for later use;
3) Mixing Solution A and Solution B while maintaining the temperature at 85° C.-95° C., and stirring to obtain a homogenous solution for later use;
4) Putting a prescription amount of dimethyl sulfoxide and a small amount of anhydrous ethanol into a container, stirring and mixing well to obtain a homogenous solution, Solution C, for later use;
5) Cooling the mixture of Solution A and Solution B to 60° C., adding Solution C to the mixture, stirring and mixing well before cooling down to room temperature, adding the remaining amount of anhydrous ethanol and mixing well;
6) Filtering with 0.45 um microporous membrane, aliquoting into 5 ml ampoules and sealing the ampoules; and
7) Sterilizing at 121° C. for 30 minutes.

The beneficial effects of the present invention are further illustrated by the following experiments.

TABLE 1

Comparison of the formulation of the present invention with that disclosed in CN1073415C

| The Present Invention | | Example 2 in CN1073415C | |
| --- | --- | --- | --- |
| p-Toluenesulfonamide | 30% | p-Toluenesulfonamide | 30% |
| PEG-400 | 30% | PEG-400 | 33.5% |
| 1,2-propanediol | 8% | 1,2-propanediol | 16.4% |
| Sebacic acid | 4% | Suberic acid | 8.2% |
| 2-ethyl-1,3-hexanediol | 15% | p-Toluenesulfonic acid | 3.7% |
| Dimethyl sulfoxide | 5% | Dimethyl sulfoxide | 6.7% |
| Anhydrous ethanol | 8% | Ethanol | 1.5% |

The present invention is an improvement on the basis of the prior art (CN1073415C). As shown in the above table, the formulation of the present invention made the following improvements as compared to the formulation disclosed in Example 2 of the Chinese patent CN1073415C:
1. Use of sebacic acid instead of suberic acid,
2. Use of 2-ethyl-1, 3-hexanediol instead of p-toluenesulfonic acid.

By making the above improvements, this invention solved a range of issues associated with the known formulation such as low stability.

The beneficial effects of the present invention are further illustrated by following studies.

Experiment 1. Study on the Chinese Patent CN1073415C

Comparative studies were conducted on injections prepared according to the examples disclosed in the CN1073415C patent.

| Raw materials | Example 1 | Example 2 |
| --- | --- | --- |
| p-Toluenesulfonamide | 30% | 40% |
| PEG-400 | 33.5% | 40% |
| 1,2-propanediol | 16.4% | 10% |
| Suberic acid | 8.2% | 3% |
| p-Toluenesulfonic acid | 3.7% | 2% |
| Dimethyl sulfoxide | 6.7% | 3% |
| Ethanol | 1.5% | 2% |
| Stability | Stored at 4° C. ± 2° C. for 10 days, crystals precipitated | Stored at 4° C. ± 2° C. for 10 days, crystals precipitated |
| LD50 | 12.54 mg/kg | 11.30 mg/kg |

Results show that crystals precipitated when the injection was refrigerated for a period of time, and this seriously affects the stability of the injection. After discovering the above problems, the inventors of this invention conducted research on the formulation and have found that the decrease in stability is likely to be caused by the presence of suberic acid and p-Toluenesulfonic acid in the formulation, for the following reasons:

The effect of PEG-400 in the formulation is as follows: acting as a water-soluble solvent to increase the compatibility of the injection with the tissues in the body.

The effect of 1, 2-propanediol in the formulation is as follow: acting as a water-soluble solvent, to increase the compatibility of the injection with the tissues in the body and inhibiting crystallization.

The effect of suberic acid in the formulation is as follows: it is a binary fatty acid and act as a fat-soluble solvent to increase the solubility of p-Toluenesulfonamide in the mixed solvent of the injection and to inhibit crystallization.

The effect of p-Toluenesulfonic acid in the formulation is as follows: it is an aromatic sulfonic acid compound, to increase the solubility of p-Toluenesulfonamide in the mixed solvent of the injection, and to inhibit crystallization.

The effect of dimethyl sulfoxide in the formulation is as follows: acting as an amphiphilic solvent to increase the solubility of p-Toluenesulfonamide in the mixed solvent of the injection, and to inhibit crystallization.

The effect of ethanol in the formulation is as follows: acting as an amphiphilic solvent to increase the solubility of p-Toluenesulfonamide in the mixed solvent of the injection, and to adjust the overall volume of the solution due to its good fluidity.

The inventors conducted the following experiments to further validate the above conclusions.

The above problems still exist when the inventor adjusted the amount of other raw materials while keeping the amount of suberic acid and p-Toluenesulfonic acid constant.

| Raw materials | Formula 1 | Formula 2 | Formula 3 | Formula 4 |
| --- | --- | --- | --- | --- |
| p-Toluenesulfonamide | 30% | 40% | 30% | 40% |
| PEG-400 | 33.5% | 40% | / | / |
| PEG-200 | / | / | 33.5% | 40% |
| 1,2-propanediol | 16.4% | 10% | / | / |
| Glycerin | / | / | 16.4% | 10% |
| Suberic acid | 8.2% | 3% | 8.2% | 3% |
| p-Toluenesulfonic acid | 3.7% | 2% | 3.7% | 2% |
| Dimethyl sulfoxide | 6.7% | 3% | / | / |
| Dimethylformamide | / | / | 6.7% | 3% |
| Anhydrous ethanol | 1.5% | 2% | / | / |
| Water for injection | / | / | 1.5% | 2% |
| Stability | Stored at 4° C. ± 2° C. for 10 days, crystals precipitated | Stored at 4° C. ± 2° C. for 10 days, crystals precipitated | Stored at 4° C. ± 2° C. for 10 days, crystals precipitated | Stored at 4° C. ± 2° C. for 10 days, crystals precipitated |

The results show that the problem still exists when the formulation is adjusted while maintaining the same amount of suberic acid and p-Toluenesulfonic acid. We further confirmed that suberic acid and p-Toluenesulfonic acid is the cause of the stability problem.

We then replaced suberic acid and p-toluenesulfonic acid.

Experiment 2. Screening Experiment

To replace suberic acid and p-Toluenesulfonic acid with a variety of substances while keeping other conditions unchanged, the screening process is as follows:

Screening Experiment

| Raw materials | Formula A | Formula B | Formula C | Formula D | Formula E | Formula F |
| --- | --- | --- | --- | --- | --- | --- |
| p-toluenesulfonamide | 30% | 40% | 30% | 40% | 30% | 40% |
| PEG-400 | 33.5% | 40% | 33.5% | 40% | 33.5% | 40% |
| 1,2-propanediol | 16.4% | 10% | 16.4% | 10% | 16.4% | 10% |
| Sebacic acid | / | / | 8.2% | 3% | / | / |
| Azelaic acid | / | / | / | / | 8.2% | 3% |
| Suberic acid | 8.2% | 3% | / | / | / | / |
| 2-ethyl-1,3-hexanediol | / | / | / | / | 3.7% | 2% |
| Hexanediol | / | / | 3.7% | 2% | / | / |
| p-Toluenesulfonic acid | 3.7% | 2% | / | / | / | / |
| Dimethyl sulfoxide | 6.7% | 3% | 6.7% | 3% | 6.7% | 3% |
| Anhydrous ethanol | 1.5% | 2% | 1.5% | 2% | 1.5% | 2% |
| Stability | Stored at 4° C. ± 2° C. for 10 days, small crystals precipitated | Stored at 4° C. ± 2° C. for 10 days, small crystals precipitated | Stored at 4° C. ± 2° C. for 10 days, no precipitates clear solution | Stored at 4° C. ± 2° C. for 10 days, no precipitates clear solution | Stored at 4° C. ± 2° C. for 10 days, no precipitates clear solution | Stored at 4° C. ± 2° C. for 10 days, no precipitates clear solution |

The results show that the use of sebacic acid instead of suberic acid or the use of 2-ethyl-1,3-hexanediol instead of p-toluenesulfonic acid can solve the problems associated with the known method. However, as the dosage in the known formulation was unscientific, the preparation method involved an excessively long dissolving process, so the two formulations were combined and the amount of each raw material in the formula were determined.

Experiment 3. Screening Experiments for the Amount of Raw Materials.

| Raw Materials | Formula I | Formula II | Formula III | Formula IV | Formula V | Formula VI |
| --- | --- | --- | --- | --- | --- | --- |
| p-Toluenesulfonamide | 30% | 40% | 30% | 25% | 30% | 40% |
| PEG-400 | 33.5% | 40% | 40% | 35% | 30% | 30% |
| 1,2-propanediol | 16.4% | 10% | 5% | 7% | 8% | 10% |
| Sebacic acid | 2% | 2% | 5% | 4% | 4% | 2% |
| 2-ethyl-1,3-hexanediol | 8% | 3% | 10% | 15% | 15% | 18% |
| Dimethyl sulfoxide | 6.7% | 3% | 5% | 7% | 5% | 0 |
| Anhydrous ethanol | 1.5% | 2% | 5% | 7% | 8% | 0 |
| Dissolution time | 8 min | 10 min | 4 min | 3 min | 5 min | 3.8 min |

Results show that, although all raw materials dissolved in Formula I and II, the time taken is relatively long while for Formula III-VI, raw materials dissolved faster and the final solution is clear and transparent.

In addition, the present invention is further compared with existing pharmaceutical injections.

Three samples were taken from each of Example 1, Example 5, Example 6, and Example 7 (i.e., Formulation III-VI) of the present invention (Labelled as Samples A-D), and three samples were taken from self-prepared Example 2 from Patent CN1073415C (Labelled as Sample E). All samples were stored at 4° C.±2° C. for 10 days and samples were observed at Day 0, Day 5, and Day 5 for crystal precipitation. Results are shown in Table 2:

TABLE 2

Comparison of crystal precipitation between Formulation III-VI of the present invention and CN1073415C Examples

| Sample | 0 Day | 5 Day | 10 Day |
| --- | --- | --- | --- |
| A1 | Clear and transparent solution | Clear and transparent solution | Clear and transparent solution |
| A2 | Clear and transparent solution | Clear and transparent solution | Clear and transparent solution |
| A3 | Clear and transparent solution | Clear and transparent solution | Clear and transparent solution |
| B1 | Clear and transparent solution | Clear and transparent solution | Clear and transparent solution |
| B2 | Clear and transparent solution | Clear and transparent solution | Clear and transparent solution |
| B3 | Clear and transparent solution | Clear and transparent solution | Clear and transparent solution |
| C1 | Clear and transparent solution | Clear and transparent solution | Clear and transparent solution |
| C2 | Clear and transparent solution | Clear and transparent solution | Clear and transparent solution |
| C3 | Clear and transparent solution | Clear and transparent solution | Clear and transparent solution |
| D1 | Clear and transparent solution | Clear and transparent solution | Clear and transparent solution |
| D2 | Clear and transparent solution | Clear and transparent solution | Clear and transparent solution |
| D3 | Clear and transparent solution | Clear and transparent solution | Clear and transparent solution |
| E1 | Clear and transparent solution | Precipitation of fine crystals | Precipitation of crystals |
| E2 | Clear and transparent solution | Precipitation of fine crystals | Precipitation of crystals |
| E3 | Clear and transparent solution | Clear and transparent solution | Precipitation of fine crystals |

As shown in the above table, Formulations III-VI of the present invention showed a significant increase in stability at 4° C. compared to self-prepared CN 1073415C Example 2. The solution is clear and transparent after 10-day storage, and no crystal precipitated.

Accelerated Stability Experiment:

Samples were taken from Example 1, Example 5, Example 6 and Example 7 (i.e., Formulation III-VI) of the present invention (Labelled as Samples A-D), and self-prepared CN 1073415 C Example 2 (Labelled as Sample E), and stored at 40° C.±2° C., 75%±5% RH. Relevant properties were assessed and results are shown in the below table:

| Sample | Test items | Day 0 | Month 1 | Month 2 | Month 3 | Month 6 |
|---|---|---|---|---|---|---|
| A | Visible foreign matter | compliant | compliant | compliant | compliant | compliant |
|   | Relevant Substance Largest Single Impurity (%) | 0.058 | 0.031 | 0.074 | 0.078 | 0.096 |
|   | Total impurities (%) | 0.136 | 0.269 | 0.294 | 0.346 | 0.401 |
|   | Content | 99.77 | 99.57 | 99.17 | 98.08 | 98.05 |
| B | Visible foreign matter | compliant | compliant | compliant | compliant | compliant |
|   | Relevant Substance Largest single impurity (%) | 0.058 | 0.078 | 0.079 | 0.086 | 0.097 |
|   | Total impurities (%) | 0.136 | 0.155 | 0.217 | 0.263 | 0.415 |
|   | Content | 99.77 | 99.61 | 99.56 | 98.70 | 98.57 |
| C | Visible foreign matter | compliant | compliant | compliant | compliant | compliant |
|   | Relevant Substance Largest single impurity (%) | 0.058 | 0.042 | 0.050 | 0.070 | 0.088 |
|   | Total impurities (%) | 0.136 | 0.137 | 0.315 | 0.391 | 0.436 |
|   | Content | 99.77 | 99.67 | 99.49 | 99.18 | 98.87 |
| D | Visible foreign matter | compliant | compliant | compliant | compliant | compliant |
|   | Relevant Substance Largest single impurity (%) | 0.058 | 0.046 | 0.074 | 0.082 | 0.085 |
|   | Total impurities (%) | 0.136 | 0.253 | 0.319 | 0.326 | 0.421 |
|   | Content | 99.77 | 99.27 | 99.10 | 98.88 | 98.81 |
| E | Visible foreign matter | compliant | compliant | compliant | compliant | compliant |
|   | Relevant Substance Largest single impurity (%) | 0.058 | 0.067 | 0.119 | 0.131 | 0.168 |
|   | Total impurities (%) | 0.136 | 0.253 | 0.571 | 0.644 | 0.850 |
|   | Content | 99.77 | 99.46 | 99.06 | 98.59 | 97.36 |

As shown in the table above, Formulations III-IV of the present invention were significantly more stable after storage at 40° C.±2° C., 75%±5% RH for 6 months compared to CH1073415C Example 2. The growth rates of single largest impurity and total impurities were slower, and there were fewer impurities. The degradation rates of the raw materials were also slower and there was less degradation for Formulations III-IV.

EXAMPLES

The following examples are included to further illustrate the present invention. It should not be regarded as a limitation on the present invention.

Example 1: Injection

| Raw materials | Percentage by weight |
|---|---|
| p-Toluenesulfonamide | 30% |
| PEG-400 | 30% |
| 1,2-propanediol | 8% |
| Sebacic acid | 4% |
| 2-ethyl-1,3-hexanediol | 15% |
| Dimethyl sulfoxide | 5% |
| Anhydrous Ethanol | 8% |

Preparation Method:
1) Putting a prescription amount of sulfonamide compound, PEG-400, and 2-ethyl-1, 3-hexanediol into a container, stirring slowly at 85° C.-95° C. to form a miscible solution, Solution A, for later use;
2) Putting a prescription amount of sebacic acid and 1,2-propanediol, into a separate container, stirring slowly at 85° C.-95° C. to form a miscible solution, Solution B, for later use;
3) Mixing Solution A and Solution B while maintaining the temperature at 85° C.-95° C., and stirring to obtain a homogenous solution for later use;

4) Putting a prescription amount of dimethyl sulfoxide and a small amount of anhydrous ethanol into a container, stirring and mixing well to obtain a homogenous solution, Solution C, for later use;
5) Cooling the mixture of Solution A and Solution B to 60° C., adding Solution C to the mixture, stirring and mixing well before cooling down to room temperature, adding the remaining amount of anhydrous ethanol and mixing well;
6) Filtering with 0.45 um microporous membrane, aliquoting into 5 ml ampoules and sealing the ampoules; and
7) Sterilizing at 121° C. for 30 minutes.

The purpose of adding anhydrous ethanol in this formulation is to control the total volume of the final solution, and further control the total drug content in the formulation. Therefore, the amount of anhydrous ethanol to be added in Step 4 should be slightly less than the prescription amount.

Example 2. Comparative Safety Test

Using mice as animal model, Example 1 of the p-toluenesulfonamide injection was compared with CN 1073415 C Example 2 by administering a single intravenous injection at the tail vein for comparative toxicity test. Results are shown below:

Animal death rate is lower for Example 1. LD50 of CN 1073415C Example 2 is 11.30 mg/kg, (95% CI=9.47-13.13 mg/kg) LD50 of Example 1 of the present invention is 18.10 mg/kg (95% CI=15.2-21.0 mg/kg). After the improvement of the current invention, i.e. replacing p-toluenesulfonic acid with 2-ethyl-1,3-hexanediol, LD50 of the drug was increased by 60% (P<0.01), significantly reducing the toxicity of the injection.

Example 3. Efficacy Experiment

Example 1 of the present invention was tested on animals. Table 2 shows the effect of intramuscular injection of Example 1 on the development of lung cancer in mice.

The results of the experiments showed that:
1) At 0.5 ml, 1.0 ml, 2 ml, and 2.0 ml/kg/d×10d, Example 1 has different levels of anti-tumor effect on mice transplanted lung tumor. Anti-tumor effect increases as dosage increases.
2) At 2.0 ml/kg/d×10d dosage, Example 1 has no anti-tumor effect on mice liver cancer and mice sarcoma S-180.
3) This demonstrates that the selected dosages of Example 1 have significant anti-tumor effect on mice lung cancer.
4) Injection of Example 1 has a high therapeutic index for mice cancer.

Example 4. Clinical Trials

Single-arm clinical trial of Example 1 injection (PTS injection) for local intra-tumoral injection in patients with severe airway obstruction due to central type lung cancer.

Clinical studies of PTS injection conducted by the Guangzhou Institute of Respiratory Diseases and 21 clinical research institutes approved by the Ministry of Health reached the following conclusions:

89 patients were enrolled in the PTS clinical trial. Of these, 10 dropped out, 7 were excluded from analysis and used only for safety assessment (either because the subjects did not meet the inclusion criteria or the investigator had a violation of clinical protocols). A total of 72 patients were included in the efficacy analysis.

Among the 72 subjects aged between 23-79, 59 were males and 13 were females. Subject statistics based on their lung cancer stage: 46 cases in IV phase, 22 cases in stage IIIb, 4 cases in stage IIIa. Subject statistics based on the location of tumor, 6 cases of airway, 28 cases of left main bronchus, 30 cases of right main bronchus, and 8 cases of right intermediate bronchus.

Results on Efficacy:
72 patients with central lung cancer after 2-4 weeks of treatment with PTS local target tumor injection:

TABLE 2

Effect of intramuscular injection of Example 1 on lung cancer development in mice

| Group | Treatment | Dosage (/kg/d × 10 d) | No. of subjects Start | No. of subjects End | Body weight Start | Body weight End | Average weight of tumor ($X \pm SD$) (g) | Tumor-inhibiting rate (%) | P value* |
|---|---|---|---|---|---|---|---|---|---|
| 1 | NS(control) | 2.0 ml | 11 | 11 | 20.7 | 27.9 | 3.52 ± 0.62 | 0.0 | >0.05 |
|   | Solvent (control) | 2.0 ml | 11 | 11 | 20.5 | 25.1 | 2.91 ± 0.58 | 17.3 | <0.01 |
|   | CTX | 18.0 ml | 11 | 11 | 20.8 | 25.0 | 1.82 ± 0.41 | 48.3 | <0.01 |
|   | Example 1 | 0.5 ml | 11 | 11 | 21.9 | 25.4 | 1.81 ± 0.25 | 48.6 | <0.01 |
|   | Example 1 | 1.0 ml | 11 | 11 | 21.3 | 25.2 | 1.46 ± 0.74 | 58.5 | <0.01 |
|   | Example 1 | 2.0 ml | 11 | 11 | 20.2 | 24.0 | 1.25 ± 0.72 | 64.5 | <0.01 |
| 2 | NS(control) | 2.0 ml | 11 | 11 | 20.4 | 27.7 | 2.49 ± 0.58 | 0.0 | >0.05 |
|   | Solvent (control) | 2.0 ml | 11 | 11 | 21.5 | 28.9 | 2.69 ± 0.56 | -8.0 | <0.01 |
|   | CTX | 18.0 ml | 11 | 11 | 21.6 | 28.8 | 1.54 ± 0.27 | 38.2 | <0.01 |
|   | Example 1 | 0.5 ml | 11 | 11 | 21.9 | 25.6 | 2.15 ± 0.87 | 13.7 | <0.01 |
|   | Example 1 | 1.0 ml | 11 | 11 | 21.0 | 25.8 | 2.00 ± 0.82 | 19.7 | <0.01 |
|   | Example 1 | 2.0 ml | 11 | 11 | 21.6 | 25.6 | 1.59 ± 0.64 | 36.1 | <0.01 |
| 3 | NS(control) | 2.0 ml | 11 | 11 | 21.0 | 27.6 | 2.51 ± 0.46 | 0.0 | >0.01 |
|   | Solvent (control) | 2.0 ml | 11 | 11 | 21.4 | 28.5 | 1.82 ± 0.74 | 27.5 | <0.01 |
|   | CTX | 18.0 ml | 11 | 11 | 21.7 | 27.4 | 1.02 ± 0.35 | 59.4 | <0.01 |
|   | Example 1 | 0.5 ml | 11 | 11 | 21.8 | 25.9 | 1.67 ± 0.95 | 33.5 | <0.01 |
|   | Example 1 | 1.0 ml | 11 | 11 | 21.1 | 25.3 | 1.43 ± 0.74 | 43.0 | <0.01 |
|   | Example 1 | 2.0 ml | 11 | 11 | 20.3 | 25.6 | 1.02 ± 0.57 | 59.4 | <0.01 |

Major efficacy index: objective response rate of intraluminal target lesion-according to RECIST: based on CT assessment, the objective response rate was 68.08% within 7 days from the last treatment, and 48.61% after 30 days from the exit period, respectively.

Major efficacy index: objective response rate of intraluminal target lesion-according to WHO standard: based on CT assessment, the objective response rate of intraluminal target lesion was 77.78% within 7 days from the last treatment, and 54.17% after 30 days from the exit period.

Major efficacy index: improvement rate on luminal tumor blockage, applying CT assessment, the improvement rate for obstruction due to luminal tumor is 70.45% within 7 days from the last treatment, and 70.47% after 30 days from the exit period.

Clinical benefit index: Compared with the baseline, the pulmonary function index FEV1 showed statistically significant improvement within 7 days after the last administration, with a rate of improvement of 34.72% and 18.06% at 30 days after the exit period; the total re-expansion rate for patients with atelectasis across different lobes was 44.44% (20/45). Arranged by the location with a descending re-expansion rate is as follows: 50.00% for the right middle lobe, 43.75% for the left lung, 42.11% for the left lower lobe, 38.46% for the right lower lobe, 35.00% for the left tongue lobe, and 25.00% for the right upper lobe.

Analysis of the overall efficacy showed that, the target lesions significantly shrink after intra-tumoral injection of PTS, with the objective response rate and luminal tumor obstruction improvement rate close to 70%; clinical benefit index FEV1 improved more than 30%, pulmonary re-expansion rate improved more than 40%. The indexes above directly showed that patients have reduced target lesions after PTS treatment, their airway obstruction improved, indicating that respiratory functions and life quality significantly improved after PTS treatment.

Results on Safety:

During the entire course of the clinical trial on the 89 subjects, none of them exhibited bone marrow suppression, gastrointestinal reactions or other commonly observed adverse reactions associated with systemic chemotherapy.

During the entire course of the clinical trial, vital signs, physical examination, blood examination, blood biochemical examination, immunology examination and electrocardiogram were monitored and showed no statistically significant changes.

This demonstrates that intra-tumoral injection of PTS had little systemic impact on the patients.

Example 5. Injection

| Raw materials | Percentage by weight |
| --- | --- |
| p-Toluenesulfonamide | 40% |
| PEG-400 | 30% |
| 1,2-propanediol | 10% |
| Sebacic acid | 2% |
| 2-ethyl-1,3-hexanediol | 18% |

Same method of preparation as Example 1.

Example 6. Injection

| Raw materials | Percentage by weight |
| --- | --- |
| p-Toluenesulfonamide | 30% |
| PEG-400 | 40% |
| 1,2-propanediol | 5% |
| Sebacic acid | 5% |
| 2-ethyl-1,3-hexanediol | 10% |
| Dimethyl sulfoxide | 5% |
| Anhydrous ethanol | 5% |

Same method of preparation as Example 1.

Example 7. Injection

| Raw materials | Percentage by weight |
| --- | --- |
| P-Toluenesulfonamide | 25% |
| PEG-400 | 35% |
| 1,2-propanediol | 7% |
| Sebacic acid | 4% |
| 2-ethyl-1,3-hexanediol | 15% |
| Dimethyl sulfoxide | 7% |
| Anhydrous ethanol | 7% |

Same method of preparation as Example 1.

What is claimed is:

1. A method of preparing a sulfonamide pharmaceutical composition comprising the steps of:
   1) Putting a prescribed amount of sulfonamide compound, PEG-400, and 2-ethyl-1,3-hexanediol into a container, and stirring slowly at 85° C.-95° C. to form Solution A;
   2) Putting a prescribed amount of sebacic acid and 1,2-propanediol into a separate container, and stirring slowly at 85° C.-95° C. to form Solution B;
   3) Mixing Solution A and Solution B while maintaining at 85° C. -95° C., and stirring well to obtain a homogenous solution;
   4) Putting a prescribed amount of dimethyl sulfoxide and a first volume of anhydrous ethanol into a container, and stirring and mixing well to obtain Solution C; and
   5) Cooling the homogeneous solution from step 3) to 60° C. before adding Solution C, stirring and mixing well before cooling down to room temperature, adding a second volume of anhydrous ethanol and mixing well to obtain said sulfonamide pharmaceutical composition;

wherein the sulfonamide pharmaceutical composition comprises the following raw materials:

| Raw materials | Percentage by weight |
| --- | --- |
| p-Toluenesulfonamide | 30% |
| PEG-400 | 30% |
| 1,2-propanediol | 8% |
| Sebacic acid | 4% |
| 2-ethyl-1,3-hexanediol | 15% |
| Dimethyl sulfoxide | 5% |
| Anhydrous ethanol | 8%. |

* * * * *